(12) United States Patent
Cave et al.

(10) Patent No.: US 10,154,628 B2
(45) Date of Patent: Dec. 18, 2018

(54) COATING METAL OXIDE PARTICLES

(71) Applicant: The Nottingham Trent University, Nottinghamshire (GB)

(72) Inventors: Gareth Wynn Vaughan Cave, Northhamptomshire (GB); Victoria Jane Mundell, Northhamptomshire (GB)

(73) Assignee: The Nottingham Trent University, Nottingham (GB)

( * ) Notice: Subject to any disclaimer, the term of this patent is extended or adjusted under 35 U.S.C. 154(b) by 264 days.

(21) Appl. No.: 14/384,605

(22) PCT Filed: Mar. 15, 2013

(86) PCT No.: PCT/GB2013/050651
§ 371 (c)(1),
(2) Date: Sep. 11, 2014

(87) PCT Pub. No.: WO2013/136082
PCT Pub. Date: Sep. 19, 2013

(65) Prior Publication Data
US 2015/0027050 A1    Jan. 29, 2015

(30) Foreign Application Priority Data
Mar. 15, 2012   (GB) .................................. 1204579.5

(51) Int. Cl.
*A01G 22/00* (2018.01)
*C05D 9/02* (2006.01)
(Continued)

(52) U.S. Cl.
CPC ............ *A01G 22/00* (2018.02); *A01G 31/00* (2013.01); *A23L 19/05* (2016.08); *A23L 33/16* (2016.08);
(Continued)

(58) Field of Classification Search
CPC ........ A01G 31/00; A01G 1/001; A01G 22/00; A61K 9/167; A61K 31/375;
(Continued)

(56) References Cited

U.S. PATENT DOCUMENTS 3,555,727 A * 1/1971 Jaquith .................. C09K 17/52
47/2
3,935,673 A * 2/1976 Robins ................... A01G 31/06
47/58.1 R
(Continued)

FOREIGN PATENT DOCUMENTS

AP            2871          3/2014
AT         121713           5/1995
(Continued)

OTHER PUBLICATIONS

ISR for PCT/GB2013/050651; Oct. 14, 2014.
(Continued)

*Primary Examiner* — Tien Q Dinh
*Assistant Examiner* — Ebony E Evans
(74) *Attorney, Agent, or Firm* — Allan Watts PLLC

(57) ABSTRACT

The invention relates to methods of forming coated metal oxide particles, suspensions of such coated particles, particles comprising functionalized surface coatings and to fortification of food crops with coated metal oxide particles. Embodiments disclosed include a method of fortifying a food crop with a trace element, the method comprising growing the food crop in a growth medium comprising the trace element in the form of metal oxide particles coated with an organic compound, and a food crop fortified with a trace element in the form of metal oxide particles. Also disclosed is a method of forming coated particles, the method comprising: providing a first quantity of metal oxide particles; providing a second quantity of a coating material
(Continued)

comprising an organic compound; and mechanically mixing the metal oxide particles with the coating material in a dry mixing process to provide a mixture comprising the metal oxide particles coated with the organic compound.

20 Claims, 10 Drawing Sheets

(51) Int. Cl.
| | |
|---|---|
| A01G 31/00 | (2018.01) |
| A61K 9/16 | (2006.01) |
| A61K 31/375 | (2006.01) |
| A61K 31/4178 | (2006.01) |
| A61K 31/7036 | (2006.01) |
| A61K 33/26 | (2006.01) |
| B05D 1/40 | (2006.01) |
| B05D 3/04 | (2006.01) |
| B05D 3/12 | (2006.01) |
| A23L 19/00 | (2016.01) |
| A23L 33/16 | (2016.01) |

(52) U.S. Cl.
CPC ............ *A61K 9/167* (2013.01); *A61K 31/375* (2013.01); *A61K 31/4178* (2013.01); *A61K 31/7036* (2013.01); *A61K 33/26* (2013.01); *B05D 1/40* (2013.01); *B05D 3/0406* (2013.01); *B05D 3/0413* (2013.01); *B05D 3/12* (2013.01); *C05D 9/02* (2013.01)

(58) Field of Classification Search
CPC ............ A61K 31/4178; A61K 31/7036; A61K 33/26; A23L 19/05; A23L 33/16; B05D 3/0406; B05D 3/0413; B05D 3/12
USPC .......................................................... 47/59 R
See application file for complete search history.

(56) References Cited

U.S. PATENT DOCUMENTS

| | | | | |
|---|---|---|---|---|
| 5,219,577 | A | | 6/1993 | Kossovsky et al. |
| 5,590,387 | A | * | 12/1996 | Schmidt ................ B22F 1/0014 419/36 |
| 6,123,920 | A | | 9/2000 | Gunther et al. |
| 7,037,962 | B2 | * | 5/2006 | Destro ........................ C08J 5/18 47/17 |
| 7,332,586 | B2 | * | 2/2008 | Franzen ................ A61K 9/5115 424/491 |
| 7,913,453 | B2 | | 3/2011 | Kerber et al. |
| 2004/0221426 | A1 | | 11/2004 | Igawa et al. |
| 2004/0253174 | A1 | * | 12/2004 | Williams ................ B82Y 30/00 423/608 |
| 2005/0126238 | A1 | | 6/2005 | Gordon |
| 2006/0245998 | A1 | * | 11/2006 | Kahn ...................... B82Y 30/00 423/592.1 |
| 2007/0227211 | A1 | | 10/2007 | McCoy |
| 2007/0292622 | A1 | * | 12/2007 | Rowley .................. B82Y 10/00 427/407.1 |
| 2009/0110644 | A1 | | 4/2009 | Margel et al. |
| 2009/0309597 | A1 | * | 12/2009 | Horak ................. A61K 49/1836 324/318 |
| 2010/0166870 | A1 | * | 7/2010 | Iyer ............................ B01J 2/14 424/490 |
| 2010/0303730 | A1 | | 12/2010 | Hegmann et al. |
| 2010/0316712 | A1 | * | 12/2010 | Nangia ................ A61K 9/0065 424/472 |
| 2011/0104073 | A1 | | 5/2011 | Zeng et al. |
| 2013/0180326 | A1 | * | 7/2013 | Lundgren ................ B05D 1/18 73/150 A |
| 2013/0219979 | A1 | * | 8/2013 | Deb ....................... C05G 3/0041 71/27 |
| 2014/0001416 | A1 | * | 1/2014 | Fiffemeier .......... H01M 4/1393 252/511 |

FOREIGN PATENT DOCUMENTS

| | | |
|---|---|---|
| AU | 2006326721 | 6/2007 |
| BR | PI0619842 | 10/2011 |
| CA | 2630642 | 6/2007 |
| CN | 101326143 | 12/2008 |
| CN | 101935013 | 1/2011 |
| DE | 69109239 | 11/1995 |
| EA | 200870054 | 10/2008 |
| EG | 24790 | 9/2010 |
| EP | 0485225 | 5/1992 |
| EP | 2004575 | 12/2008 |
| ES | 2071934 | 7/1995 |
| IL | 191634 | 6/2014 |
| JP | 05255111 | 10/1993 |
| JP | 4729120 | 7/2011 |
| MA | 30051 | 12/2008 |
| UA | 94249 | 4/2011 |
| WO | 2007068348 | 6/2007 |
| WO | 2013136082 | 9/2013 |

OTHER PUBLICATIONS

GBA Search Report under Section 17(5) for application No. GB1204579.5; dated Jul. 6, 2012.

Database WPI Week 201131 Thomson Scientific, London, GB; AN 2011-B64893 XP002730605, & CN 101 935 013 A (Nat Cent Nanoscience & Technology China); Jan. 5, 2011.

Database WPI Week 201149 Thomson Scientific, London, GB; AN 2011-J33226 XP002698861, & JP 47 29120B B (Honda Motor Co Ltd); Jul. 20, 2011.

* cited by examiner

COATING METAL OXIDE PARTICLES

CROSS-REFERENCE TO RELATED APPLICATIONS

This application is a national stage application under 35 U.S.C. 371 of and claims priority to International Application No. PCT/GB2013/050651, filed Mar. 15, 2013, which claims priority to Great Britain Application No. 1204579.5 filed on Mar. 15, 2012. International Application No. PCT/GB2013/050651 and Great Britain Application No. 1204579.5 are incorporated herein by reference.

FIELD OF THE INVENTION

The invention relates to methods of forming coated metal oxide particles, suspensions of such coated particles, particles comprising functionalised surface coatings and to fortification of food crops with coated metal oxide particles.

BACKGROUND

Nanoparticles, i.e. particles having dimensions in the general range of around 1 nm to 100 nm, have a myriad of actual and potential uses in many different fields of science and technology, ranging from electronic and structural materials engineering to medical technology. A particular feature of such particles is the high ratio of surface area to volume (an inherent feature of particle size), which can be exploited in applications where surface activity is important, although this also causes problems when handling and maintaining such particles in suspension. Stable suspensions of certain types of nanoparticles have however been known for many years, one of the earliest such examples being suspensions of gold nanoparticles. Such particles can be used in applications such as medical imaging, where a fine dispersion of a high atomic weight material can be used as an effective contrast agent, for example in X-ray imaging applications.

Superparamagnetic iron oxide (SPIO) is an example of a material available in nanoparticulate form, typically comprising nanocrystalline particles with dimensions ranging from 2 nm to 100 nm in diameter. This material has been utilised in recent years for various applications including in magnetic inks, biosensors, catalysis, magnetic-activated cell sorting and in targeted drug delivery.

The paramagnetic properties of SPIO nanoparticles are also being used and developed as contrast agents for magnetic resonance imaging (MRI). SPIO nanoparticles have a particular advantage as MRI contrast agents due to their low toxicity, particularly in comparison with existing contrast agents based on gadolinium, since iron becomes incorporated into the body to make haemoglobin upon degradation. Gadolinium-based contrast agents have a disadvantage of potential severe side effects including nephrogenic fibrosing dermopathy and other conditions. This has led to products finding their way to the market based on SPIO nanoparticles in preference to gadolinium-based agents for bowel, liver and spleen imaging. Other applications are also expected to be developed and used in the near future.

SPIO, as with most other metal oxides, is inherently insoluble in water and other solvents. The surfaces of particles of such materials can however, be treated to allow a stable colloidal suspension to be formed. Treating the surfaces of nanoparticles is commonly known as functionalising or capping. Suitably functionalised nanoparticles become effectively soluble (although the core metal oxide particle will remain undissolved), which allows for use of the particles in biomedical applications where compatibility with aqueous solvents is essential. Creating such suspensions is therefore also known as solubilising, and the suspensions are also referred to as solutions.

Current known methods for solubilising SPIO nanoparticles can involve adding a polysaccharide such as dextran as a coating agent in situ, with the coating agent being added in solution to a suspension of nanoparticles. Coating, or capping, of the particles may occur during their formation, although hydrophobic groups have also been used. Capped particles can be further functionalised for various applications such as drug delivery, diagnosis and therapy. A self-assembled monolayer (SAM), can also be formed via the addition of a functionalising group such as sulfonic or phosphonic acids, or the ferrofluid (a term for a colloid of magnetic particles in a liquid solvent) can be taken up into a liposome to form a magneto-liposome.

Elevated temperatures of up to around 260° C. are currently used to form capped SPIO nanoparticles. This can be problematic as the temperatures required limits the capping groups that can be used to those that are stable at high temperatures, thus eliminating many potential bioactive compounds. Furthermore, other methods may also lead to the requirement of additional functionalising steps and/or ligand exchange in order to solubilise the particles. This can be complex and time-consuming due to the use of additional processing steps. The required linking compounds may also lead to an increase in toxicity and thus limitations in applications, particularly in biomedical applications.

A further problem with forming coatings on nanoparticles during either formation or in subsequent solution processing is that the resulting nanoparticle suspension can have a limited shelf life, and may settle out of suspension over an extended period of time.

Iron is an important micronutrient, found in nearly all forms of life on the planet, ranging from evolutionarily primitive archaea to more complex organisms such as plants and humans. It has been estimated that 30% of the world wide population is deficient in this element. Iron deficiency in humans arises when the physiological requirements cannot be met by Fe absorption from the diet and results in the reduction of both circulating haemoglobin and essential iron-containing enzymes such as catalase. The main consequences of these are: reduced psychomotor and mental development in infants, decreased immune function, poor work performance and tiredness. The most common strategy for decreasing micro-nutrient malnutrition is supplementation with pharmaceutical preparations, however this method is expensive and its viability as a long term strategy is heavily dependent on continued funding, infrastructure and a good distribution network, which cannot be guaranteed in poorer countries where iron deficiency is most prevalent.

The current method for improving iron concentration in plants is based on the addition of iron-containing fertilisers to the soil. However, this approach is very limited due to solubility issues of iron oxide, resulting in little impact on increasing iron levels in healthy plants. Recent research into fortifying iron in plants has been largely focussed on genetic engineering or other ways of improving the bioavailability of iron in the plant. Though studies into the genetic engineering of plants have shown some results, the large legislative issues and ethical concerns surrounding the implementation of genetically modified crops on a commercial scale means there is a need for alternative routes to fortification of food crops with iron.

It is an object of the invention to address one or more of the above mentioned problems.

SUMMARY OF THE INVENTION

In accordance with a first aspect of the invention there is provided a method of forming coated particles, the method comprising:

providing a first quantity of metal oxide particles;
providing a second quantity of a coating material comprising an organic compound; and
mechanically mixing the metal oxide particles with the coating material in a dry mixing process to provide a mixture comprising the metal oxide particles coated with the organic compound.

It has been found that a dry mechanical mixing process is surprisingly effective at forming coated metal oxide particles, particularly for SPIO nanoparticles. The resulting coated particles can be readily dispersed following the dry mixing process in a solvent such as water, and the resulting dispersion can remain stable for long periods. The dry mixing route also allows the resulting mixture to be used as a starting point for further processes, and can be stored in a dry form until a dispersion is required. This leads to a significant advantage in terms of the long term storage of such coated particles, since some compounds used as functionalising agents can be unstable over extended periods in solution. The benign nature of the process, coupled with its wide potential applications, in particular when applied to aqueous solutions, make the process a desirable alternative to existing equivalent processes for providing coated particles.

Further advantages of the mixing process include a reduced energy input, reduced waste and improved efficiency, thereby providing a more environmentally friendly or benign process for making coated particles compared with existing technologies.

In certain preferred embodiments, the metal oxide comprises or consists of iron oxide, which in nanoscale form is known as superparamagnetic iron oxide (SPIO). The iron oxide may be in the form of magnetite ($Fe_3O_4$) or haematite ($Fe_2O_3$). In other variants, the iron oxide may be mixed with tin oxide, an advantage of which is that a mixture of iron and tin oxide provides contrast for X-Ray as well as magnetic resonance imaging. An exemplary ratio of iron to tin in such a mixture is 2 parts iron to 1 part tin by atomic weight, i.e. in a stoichiometric ratio $Fe_2SnO_4$. Other metal oxides may alternatively be used.

The dry mixing process may for example comprise applying shear to mix together the metal oxide particles and the coating material. The process may comprise grinding or milling the mixture, for example in a mortar and pestle or other type of rotary milling or grinding process. Other mechanical mixing processes may be used, such as ball milling, twin roll milling or twin screw mixing. A common feature of such processes is the application of high levels of shear to the dry powder mixture, which acts to distribute the organic compound among and around the metal oxide particles and allows the surfaces of the particles to interact and bond with the organic compound to form the desired coated particles.

The dry mixing process is preferably performed at a temperature of less than 100° C., optionally less than 60° C., and further optionally at or around ambient temperature (for example at or around 5° C., 10° C., 15° C., 20° C., 25° C., 30° C. or any range within these temperature values). Lower temperatures are particularly advantageous when applying organic coating compounds that may become unstable or decompose at elevated temperatures.

The coating material may comprise or consist of an organic compound selected from one or more of an amino acid and a peptide. Other organic compounds including vitamins and pharmaceuticals may also be used. In a particular exemplary embodiment, iron oxide nanoparticles are mixed and coated with ascorbic acid (vitamin C). The resulting dry mixture can be used as a food supplement to add both iron and vitamin C, which are known to advantageously work together to enhance take-up of iron into the body. Other dry mixtures comprising a trace mineral in the form of a metal oxide particle coated, or functionalised, with an organic compound such as a vitamin, may be used as a food supplement. A further exemplary mixture is calcium with vitamin B12 (cobalamin) and or vitamin D3 (cholecalciferol), where calcium is in the form of calcium oxide particles.

The organic compound preferably comprises one or more of a carboxyl, hydroxyl, amine or phosphate functional group, which function to bond the organic compound to the surface of the metal oxide particles by electrostatic bonding. Carboxyl and amine groups are particularly preferred, as these are effective at forming such bonds.

The method may further comprise a step of dispersing the mixture, following the dry mixing process, in a solvent to provide a colloid of the particles in the solvent. The resulting colloid can be used immediately or can be stored for future use, as the colloid will generally remain stable for extended periods.

The solvent used to disperse the mixture is commonly a polar solvent such as water, although in certain applications other solvents may be used such as chloroform. Water is generally preferred for biomedical applications, due to the requirement for compatibility with aqueous biological systems.

The method may further comprise a step of a wet mixing process following addition of the solvent, in order to more effectively disperse the mixture in the solvent, the wet mixing process optionally comprising applying mechanical shear across the mixture. To make the application of mechanical shear more effective, the solvent may be added in more than one stage, with a mixing process applied after a first amount is added to form a paste, followed by addition of further solvent to obtain a final desired strength of dispersion.

Following solvent addition, and optional further mixing, the method may further comprise a filtering step for filtering the resulting colloid. The filtering step may be necessary to ensure that particles above a certain size are removed from the dispersion. The filtering step may for example remove particles above 200 nm from the dispersion. Alternatively, or additionally, a settling step, typically centrifugation may be used to remove such large particles. Such particles will generally be agglomerations of smaller particles that have not been broken down and coated during the preceding mixing processes.

For magnetic particles such as SPIOs, unbound coating material may be separated from the particles (both coated and uncoated) by magnetic separation. In an exemplary separation process, the mixture of particles and coating material may be suspended in a solvent in which none of the mixture is soluble and the suspension passed through a tube (preferably with a bore of around 1.5 mm in diameter or smaller), the tube being wrapped around or otherwise in close proximity to a magnetic field, the magnetic field for example being as provided by a neodymium iron boride magnet. The solvent is then passed over the mixture through the tube, with the result being that the coated and uncoated particles are attracted to the magnet and adhered to the inside the tube and the flow of solvent removing unbound material from the mixture. A solvent in which the coating material is soluble, such as water, is then passed through the tube, thereby solubilising the coated particles which can be collected on their own. The uncoated particles can then be removed from the magnet and extracted from the tube ready to be recycled. A solvent free method may also be used, for example by using air flow rather than a solvent for the first step of the separation process.

The particles preferably have a volumetric mean particle size of between 2 nm and 1 micron in diameter, and further preferably between 2 nm and 100 nm in diameter, as measured for example by methods such as dynamic light scattering, disc centrifuge analysis or transmission electron microscopy. A further preferred volumetric mean particle size range is between 2 nm and 50 nm, or optionally between 2 nm and 20 nm.

A preferred ratio of the particles to the coating agent is between around 1:0.5 and around 1:2 by mass, with a further preferred ratio in the region of 1:1, i.e. approximately equal quantities of metal oxide to coating material by mass. This range of mixing ratios is preferred because the content of metal oxide in suspension decreases with an increasing mass of coating material, due to mixing effects.

The method according to the first aspect of the invention may further comprise a step of dispersing the coated metal oxide particles in a polymer precursor followed by polymerisation of the polymer precursor.

According to a second aspect of the invention there is provided a dry or solvent-free mixture of metal oxide particles and a coating material comprising an organic compound, wherein the metal oxide particles are coated with the organic compound. The dry mixture is preferably the result of the mechanical mixing process according to the first aspect of the invention.

The term 'dry mixture' is intended to encompass mixtures that are substantially free of any solvents, at least to the extent that the mixture is friable and not in a liquid or paste form. The dry mixture may be in a free-flowing powder form, for example comprising particles formed of agglomerations of the particles coated with the organic compound. The organic compound preferably comprises one or more functional groups selected from a carboxyl, hydroxyl, amine or phosphate group. The organic compound is preferably electrostatically bonded to the particle surfaces by the one or more functional groups. In some embodiments, however, the mixture may be solvent-free but in a liquid form, for example glycerol can be used in its liquid form at room temperature as a coating material.

An advantage of the dry or solvent-free mixture of particles and coating material is that the mixture is more stable over time compared with existing suspensions of coated nanoparticles. The dry mixture can be readily redispersed in water or another solvent when required, which is enabled by the particles being already coated with the organic compound. The dry mixture also allows for a greater degree of control over the concentration of a dispersion made with the mixture. A further advantage compared to some mixing processes is the avoidance of use of harmful solvents, and the avoidance of the need to dispose of such solvents. A yet further advantage is that a resulting dispersion can be more effective, for example as an MRI contrast agent, because use can be made of the dynamic balance between the organic compound and the solvent in which the mixture is suspended. This dynamic balance also allows the mixture to be used as a delivery system for drugs and other compounds into the body, as the electrostatic bonding between the organic compound allows for the compound to disassociate from the nanoparticles over time.

The dry mixture may comprise the metal oxide particles and coating material in a ratio of between around 1:0.5 to around 1:2.5 by weight. This preferred range allows for the coating material comprising the organic compound to be distributed around the particles so that the coating around the particles is maximised. In certain embodiments the ratio is around 1:1, for example between 1:0.9 and 1:1.1.

The organic compound may be selected from one or more of an amino acid, a vitamin such as ascorbic acid or vitamin B12, a peptide, a pharmaceutical compound, fatty acids such as palmitic acid or a fluorescent marker, such as fluorescein or rhodamine B dyes. The metal oxide may for example be iron oxide or calcium oxide. The coating material may for example comprise an antibiotic such as Neomycin or Nitrofurantoin, to provide a mixture having antibiotic properties.

According to a third aspect of the invention there is provided a food product fortified with a trace mineral in the form of metal oxide particles having a coating of a vitamin, wherein the metal oxide particles are functionalised by the vitamin bonded directly to the metal oxide particle surfaces. In an exemplary embodiment the metal oxide is iron oxide and the vitamin is ascorbic acid (vitamin C), the iron oxide particles functionalised by ascorbic acid bonded directly to the iron oxide particle surface. An advantage of this aspect of the invention is that the trace mineral and the vitamin, being in close proximity, can work together to improve the take-up of each in the body. In the exemplary embodiment of iron with vitamin C, the iron is expected to be more readily absorbed due to the close proximity of the ascorbic acid (vitamin C), as well as being provided in a very finely divided, and therefore more digestible, form. In another embodiment, calcium oxide particles may be functionalised with a coating of vitamin B12 (cobalamin).

According to a fourth aspect of the invention there is provided a method of fortifying a food crop with a trace element, the method comprising growing the food crop in a growth medium comprising the trace element in the form of metal oxide particles coated with an organic compound.

An advantage of the method of fortifying a food crop using coated metal oxide particles is that it avoids the need for genetic modification of the crop, and that the particles can be drawn into the crop without harming it, and in some cases having beneficial effects such as an increase in the quantity of starch for potatoes. The method may therefore be a cost effective way of introducing additional trace elements into existing crops such as potatoes and other staple crops by means of a straightforward application of a feed solution.

According to a fifth aspect of the invention there is provided a food crop fortified with a trace element in the form of metal oxide particles.

The trace element is preferably iron, and the metal oxide particles iron oxide particles, although other trace elements such as selenium, magnesium or zinc may alternatively or additionally be used. Iron oxide is particularly beneficial, as it can be used to fortify crops that are naturally low in iron, such as potatoes. Iron oxide particles have also been shown to have a surprising additional effect of increasing the quantity of starch in the food crop.

The metal oxide particles may have a volumetric mean particle size of between 2 nm and 1 µm in diameter, and optionally between 2 nm and 100 nm in diameter. The particles are preferably sufficiently small to be readily dispersed and drawn up through the roots of the plant and stored in the crop.

The organic compound may be selected from one or more of an amino acid, a vitamin, a peptide and a pharmaceutical compound.

In particular preferred embodiments, the organic compound comprises an amino acid, for example selected from one or more of glutamic acid, glycine, histidine and alanine. Other amino acids may alternatively be selected.

In particular preferred embodiments, the food crop is a tuberous crop such as potato (genus *solanum*, preferred species *solanum tuberosum*).

The food crop may be grown hydroponically, where the metal oxide particles are provided as a suspension in a feed solution.

DETAILED DESCRIPTION

Aspects and embodiments of the invention are described in further detail below by way of example and with reference to the enclosed drawings in which.

Figure 7A:
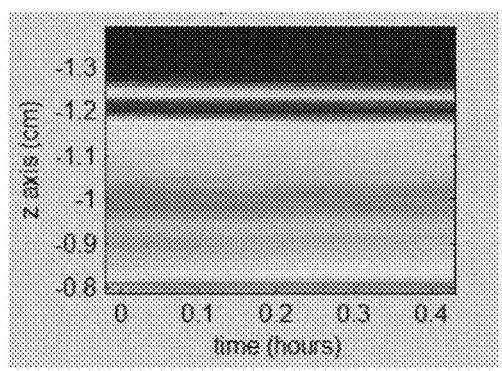
Figure 7B:
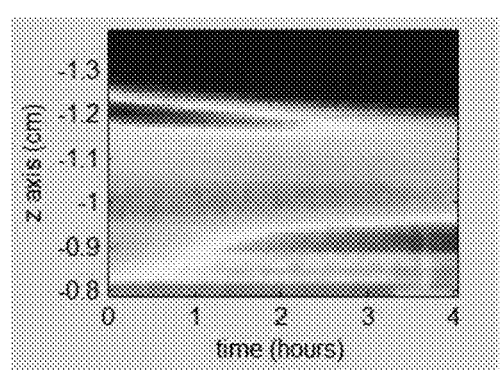

FIGS. 7a and 7b are a pair of $T_2$ relaxation plots showing permeation of liposome-encapsulated SPIO particles coated with vitamin C through porcine skin over 0-40 minutes (FIG. 7a) and 0-4 hours (FIG. 7b).

Figure 8A:
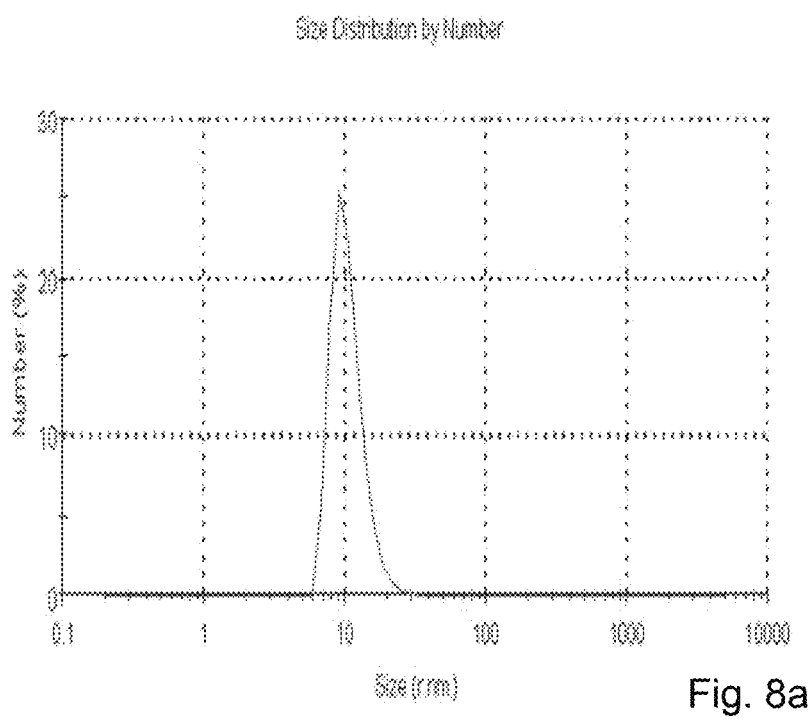
Figure 8B:
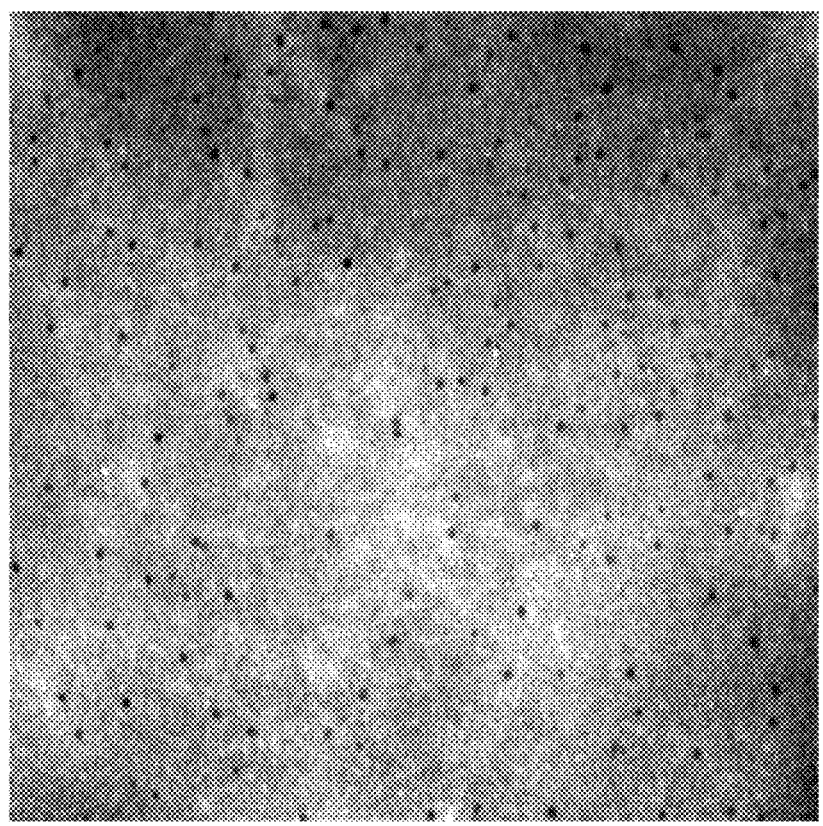
Figure 8C:
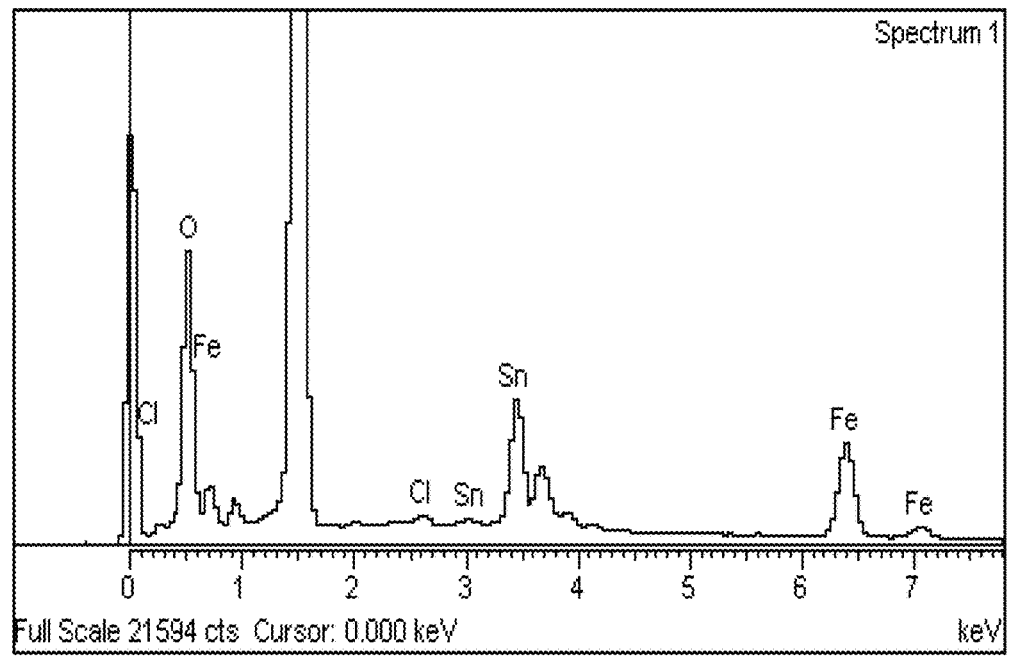
Figure 9:
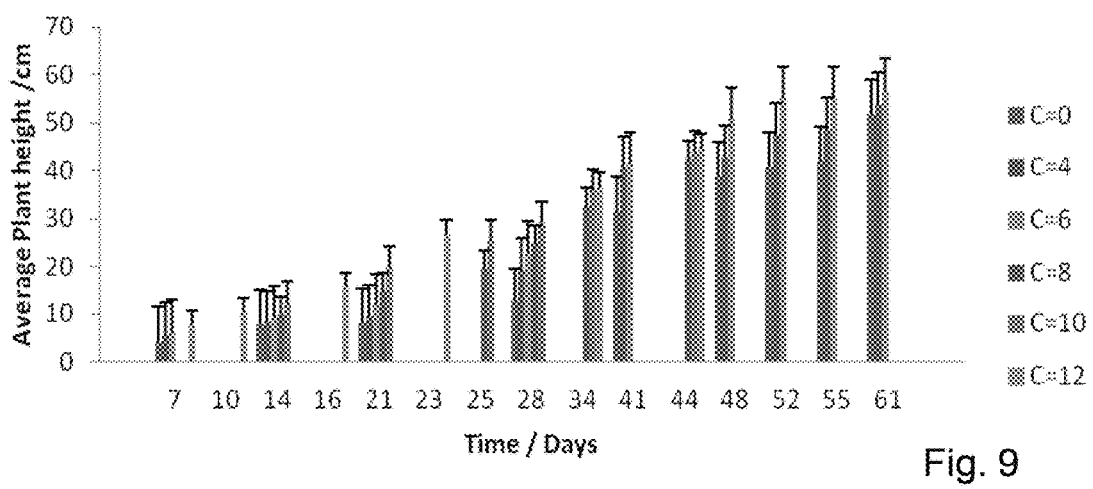
Figure 10:
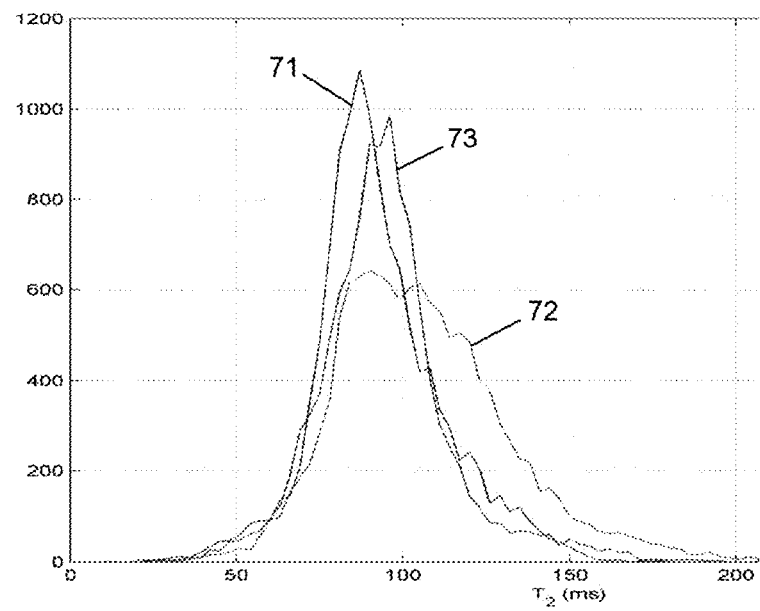
Figure 11:
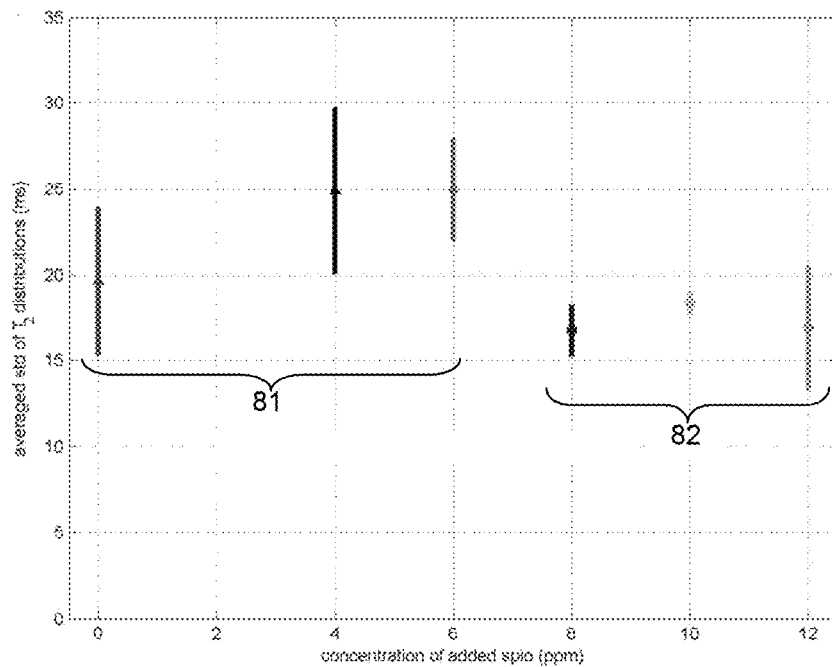
Figure 12:
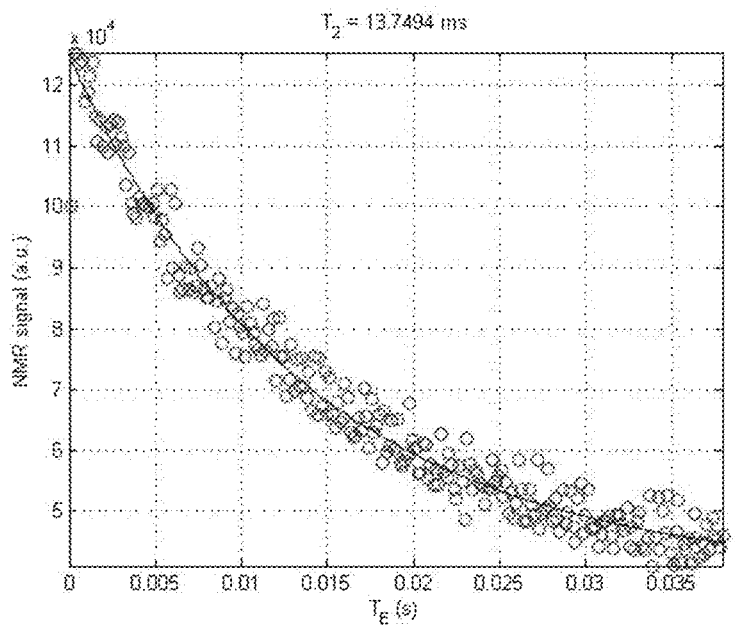
Figure 13:
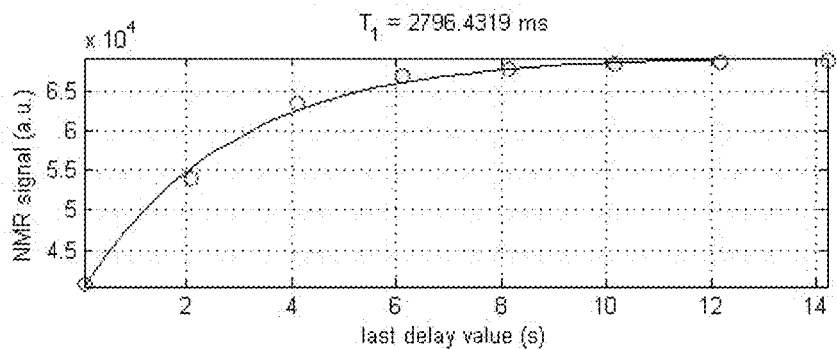
Figure 14:
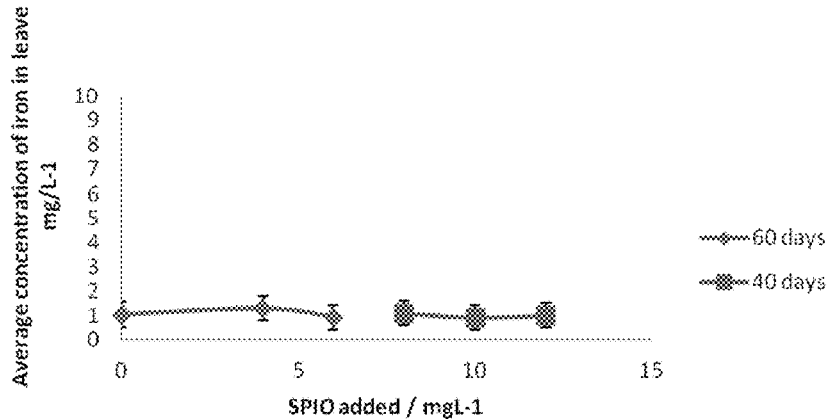
Figure 15:
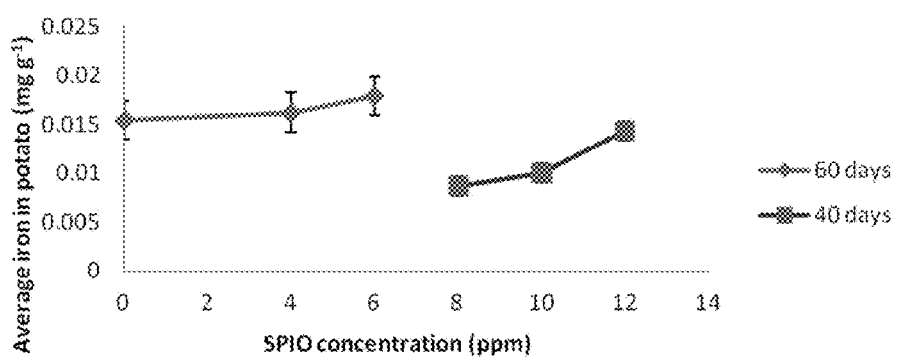
Figure 16:
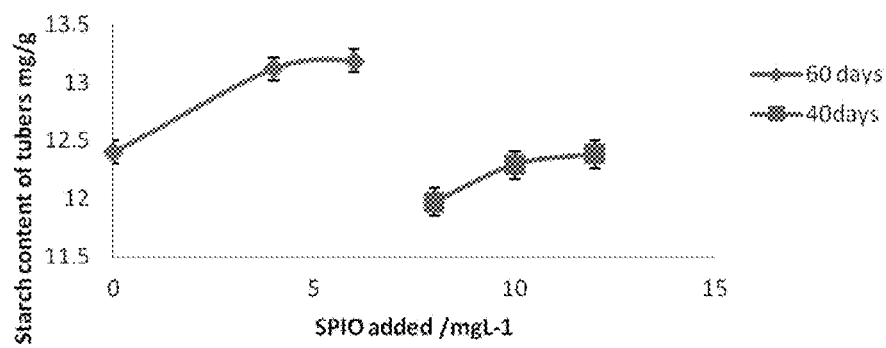
Figure 17:
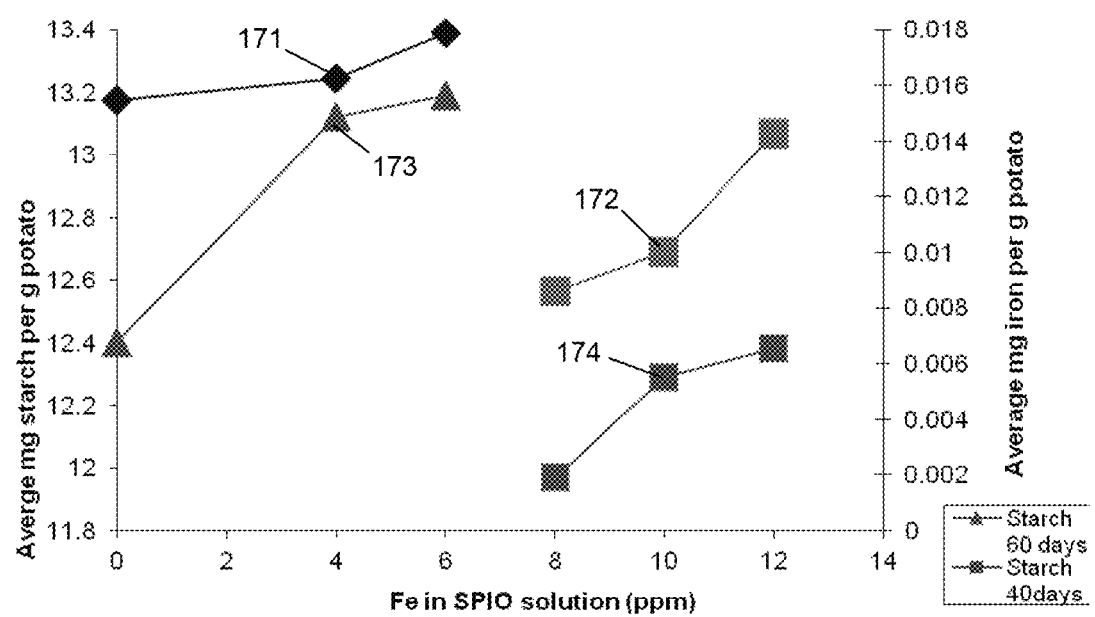

FIG. 8a is a dynamic light scattering plot showing the size distribution of iron oxide-tin oxide nanoparticles coated with fluorescent cell-penetrating peptide (RhodamineB-Gly-Arg-Lys-Lys-Arg-Arg-Gln-Arg-Arg-Arg-OH) in aqueous dispersion;

FIG. 8b is a transmission electron micrograph of the same particles after sample preparation by evaporation on carbon-coated copper TEM grid;

FIG. 8c is a TEM-EDX (energy dispersive X-ray spectroscopy) plot showing the elemental composition of these particles;

FIG. 9 is a plot of average plant height for varying concentrations of iron oxide nanoparticles as a function of growth time;

FIG. 10 is a plot of $T_2$ relaxation time for tuber samples grown in solutions having varying levels of iron oxide nanoparticles;

FIG. 11 is a plot of $T_2$ relaxation time as a function of concentration of added iron oxide particles and for different growth times;

FIGS. 12 and 13 are $T_2$ and $T_1$ relaxation times respectively for a feed solution after a complete growth cycle;

FIG. 14 is a plot of average concentration of iron in the leaves of sample plants as a function of iron oxide particle concentration, for different growth times;

FIG. 15 is a plot of average iron content in potato tubers as a function of iron oxide particle concentration, for different growth times;

FIG. 16 is a plot of average starch content of potato tubers as a function of iron oxide particle concentration, for different growth times; and FIG. 17 is a combined plot of average starch content and iron content as a function of iron oxide particle concentration, for different growth times.

The following provides a detailed description of specific exemplary embodiments relating to iron oxide nanoparticles functionalised with various organic compound coatings. Similar methods may however also apply to other metal oxide nanoparticulate materials.

A suitable starting material used in each of the following exemplary embodiments is freshly prepared SPIO nanoparticles, prepared by methods that are described in more detail by Khalafalla et al. (Khalafalla, S. E.; Reimers, G. W., *IEEE Trans. Magn.,* 1980, 16, 178), and by Kim et al. (Kim, E. H.; Lee, H. S.; Kwak, B. K.; Kim, B., *J. Magn. Magn. Mater.,* 2005, 289, 328-330). In an exemplary embodiment, to $FeCl_2.4H_2O$ (10 g, 0.05 mol) was added $FeCl_3.6H_2O$ (24.3 g, 0.09 mol) both dissolved in distilled water (100 ml). $NH_3$ solution (50 ml, 35%, 0.90 mol) was added dropwise with stirring (ca. 5 minutes) then sonicated in a sonic bath (1 hour). The mixture was filtered using a sintered funnel and washed (2×50 ml distilled water, 2×50 ml diethyl ether) and allowed to dry in air. This process resulted in 10.8 g of particles, giving a yield of 93.3%. The size of the resulting particles was measured to be around 8-10 nm by TEM when suspended in ethanol. The particles were of solid black appearance, and responded to magnetic stimulus.

In a first set of examples, dry SPIO nanoparticles were mixed with an equal weight of an amino acid previously recrystallised from 4 M aqueous HCl. Recrystallisation from hydrochloric acid in general tends to increase the solubility of the resulting coating material in water. The amino acid was ground with the SPIO for 5 minutes in an agate mortar. The resultant homogeneous brown powder was then taken up into distilled water and passed through a 0.2 μm pore microfilter. The concentration of SPIO in the solution was analysed by inductive coupled plasma (ICP). All solutions were diluted with distilled water to a concentration of 50 ppm of Fe. The $T_1$ and $T_2$ relaxation times were measured using a low field NMR method as described by Kim et al.

For amino acids and peptides presenting aqueous solubility problems, the coating agent (2 g) was first dissolved in aqueous HCl (4 M, 20 ml) aided by vortex. Solvent was then removed in vacuo to yield a dry white crystalline powder. For amino acids around 10 mbar or less pressure and 60° C. was used. For peptides 40° C. and around 10 mbar or less was used or alternatively acetone was added and kept at −20° C. for 24 hours. The resulting mixture was then centrifuged (10 minutes, 3000 rpm), the supernatant removed and the solid product washed with diethyl ether (3×50 ml), followed by drying in air or by freeze-drying.

In a specific example, 0.1 g of SPIO and 0.1 g of coating agent were ground in a mortar for 5 minutes. 2 ml of distilled water was then added to the mixture and further grinding carried out for 5 minutes. A further 3 ml of distilled water was then added and the mixture homogenised.

To separate the coated SPIO nanoparticles from the coating agent dissolved in the solvent, size exclusion chromatography was carried out using Sephadex G-50 gel filtration medium (GE Healthcare Bio-Sciences AB). This process is suitable for single amino acid coatings, peptide coated particles being less suitable due to the particles becoming stuck on the column. For such larger coatings alternative methods such as those described in the above referenced publications.

Table 1 below indicates the different values for $T_1$ and $T_2$ for SPIO nanoparticle suspensions with various different amino acid coatings. This data indicates that amino acids with basic side chains (R, H and K) tend to be more effective negative contrast agents, leading to shorter proton relaxation times. Amino acids with hydrophobic side chains tend to be less effective, having longer relaxation times. Those with side chains containing sulphur behaved in a manner that does not appear to fit any pattern. It is postulated that the sulphur atoms react to form disulphide bridges which cause excess aggregation leading to the SPIOs having different properties to those with other amino acids, thus affecting the $T_1$ and $T_2$ relaxation times.

TABLE 1

A comparison of measured $T_1$ and $T_2$ NMR relaxation times for a range of amino acid coatings applied to SPIO nanoparticles (errors for tryptophan and histidine could not be collected, and errors for $T_1$ of cysteine were out of the measurement range of the instrument, probably due to the formation of sulphur bridges).

| Amino Acid | $T_1$ (ms) | $T_2$ (ms) |
|---|---|---|
| Hydrophobic, Non-polar | | |
| Alanine (A) | 62.0 | 9.5 |
| Valine (V) | 15.7 | 3.1 |
| Leucine (L) | 72.4 | 7.9 |
| Isoleucine (I) | 56.9 | 8.3 |
| Proline (P) | 16.5 | 3.7 |
| Methionine (M) | 1.9 | 1.0 |
| Phenylalanine (F) | 75.1 | 7.9 |
| Tryptophan (W) | 180.3 | 5.3 |
| Hydrophilic, Polar | | |
| Threonine (T) | 31.0 | 7.0 |
| Cysteine (C) | 1871.0 | 1954.6 |
| Asparagine (N) | 124.7 | 7.3 |
| Glycine (G) | 92.9 | 7.4 |
| Serine (S) | 52.3 | 8.8 |
| Glutamine (Q) | 51.5 | 8.4 |
| Tyrosine (Y) | 65.9 | 4.5 |
| Acidic | | |
| Aspartic Acid (D) | 35.8 | 5.5 |
| Glutamic Acid (E) | 18.2 | 3.9 |
| Basic | | |
| Lysine (K) | 58.9 | 8.5 |
| Arginine (R) | 12.6 | 3.4 |
| Histidine (H) | 11.0 | 3.7 |

This indicates that generally as $T_1$ increases, so does $T_2$. This holds true with the exception of tryptophan, which demonstrated an increase in $T_1$ corresponding with a decrease in $T_2$ relative to the other samples. This may have been due to the hydrophobic nature of the amino acid, confirmed by the observation in the sample of a significant amount of aggregation and sedimentation.

Figure 1:
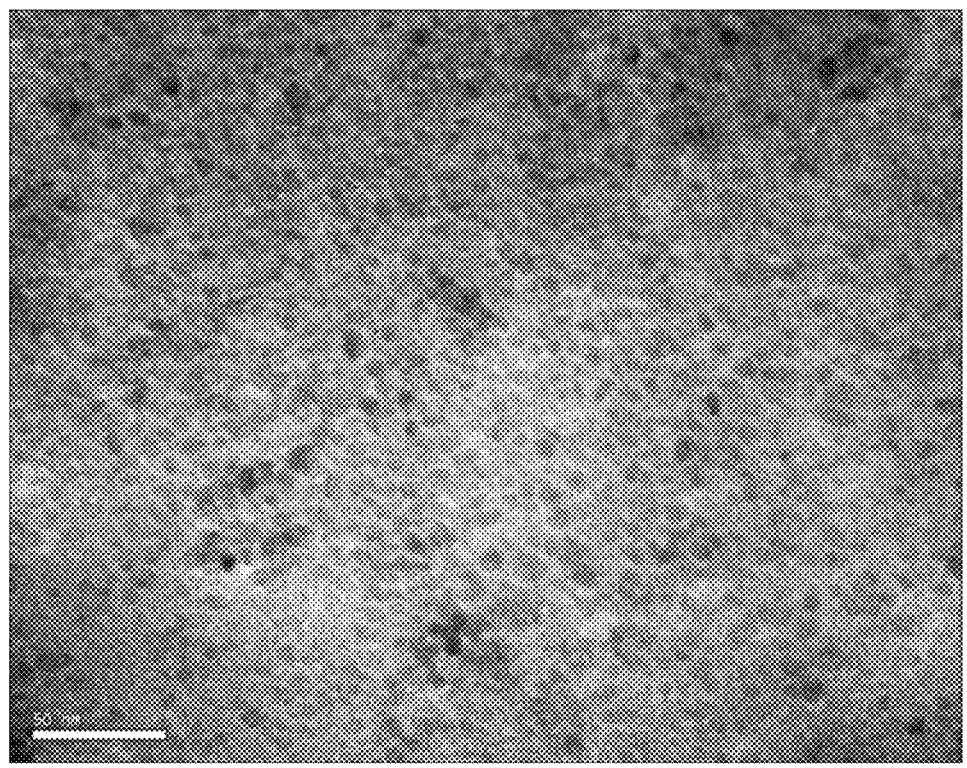
FIG. 1 is a transmission electron micrograph of glutamic acid coated SPIO nanoparticles (scale bar=50 nm)
Figure 2:
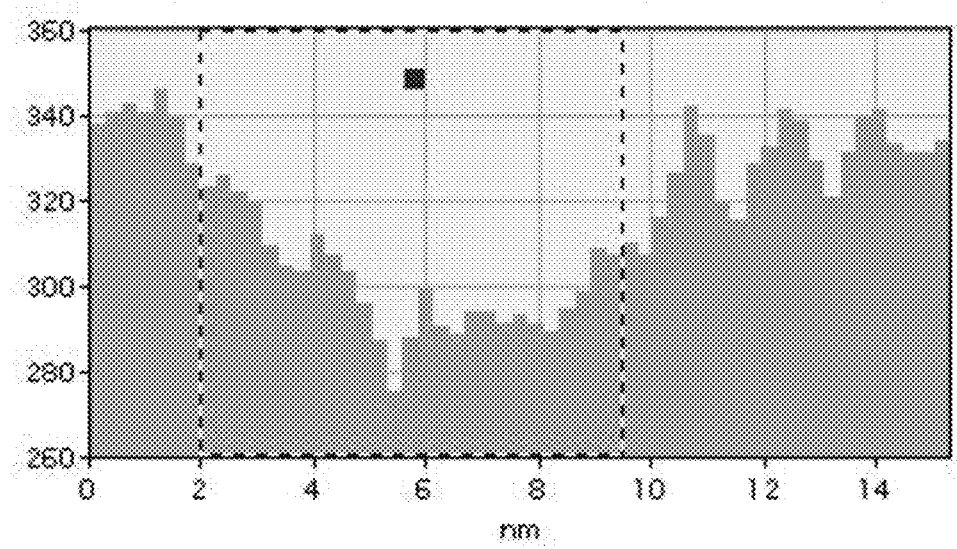
FIG. 2 is a depth profile across a single nanoparticle in the micrograph of FIG. 1, indicating a nanoparticle diameter of around 8 nm.

The particle size of each type of coated SPIO was determined by dynamic light scattering (DLS) and by transmission electron microscopy (TEM). FIG. 1 is a transmission electron micrograph of SPIO nanoparticles coated with glutamic acid. FIG. 2 is a profile across one particle, where the x-axis is a linear trace across the particle in nm and the y axis indicates relative intensity. Analysis by transmission electron microscopy indicated that the particles were around 8-10 nm in diameter, with a fairly uniform coating of amino acid of between 0.5 and 1 nm in thickness. Analysis by DLS tended to be in general agreement with TEM analysis, although with larger particles identified by DLS, apparently due to the formation of aggregates. Most of the nanoparticles were observed as single units although some were found in clusters depending on the degree of aggregation, with aggregation of nanoparticles leading to larger particles of around 20 nm-60 nm.

Thermogravimetric analysis (TGA) indicated that amino acid coverage of the particles varied from around 30% to around 90% by mass. It is postulated that this non-uniformity is due to the properties of the capping agents leading to multi-layering of the amino acid onto the SPIO particles, possibly a result of the mechanical mixing process. Further experimentation may determine whether this is the case, or if further modification of the method can lead to a greater uniformity of layer formation.

Figure 3:
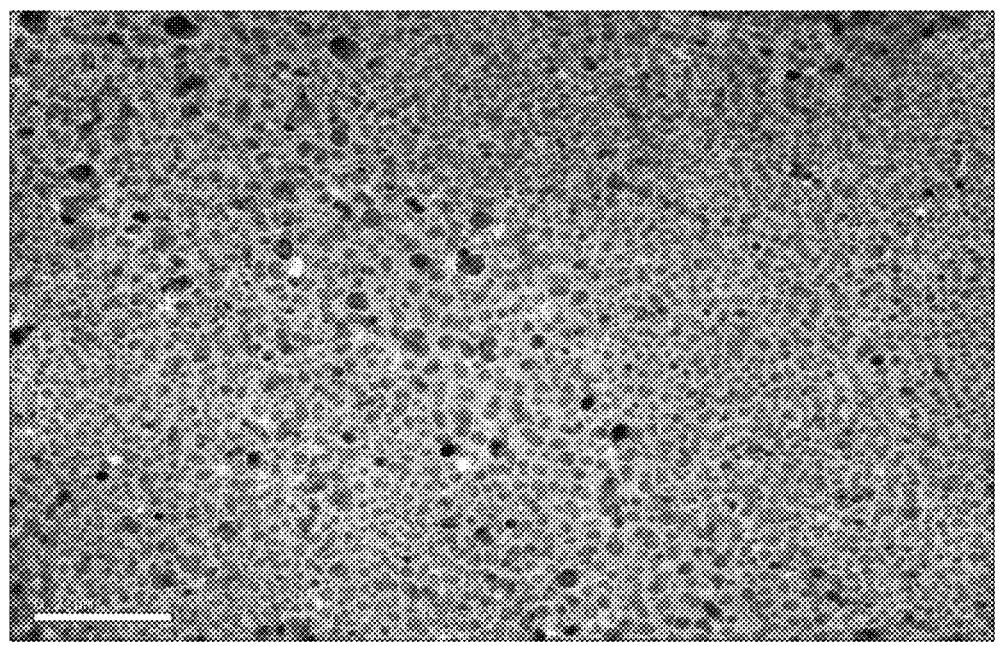
FIG. 3 is a transmission electron micrograph of vitamin C coated SPIO nanoparticles after autoclaving (the marker indicates 0.2 μm)
Figure 4A:
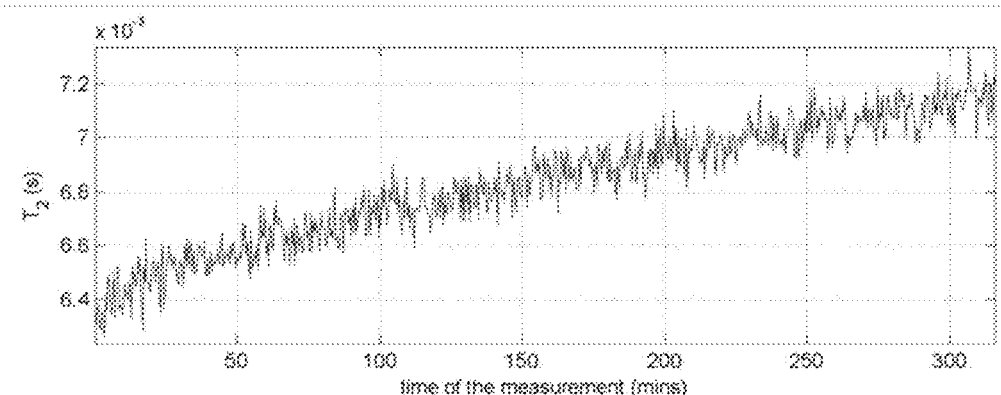
FIGS. 4a and 4b are plots of relaxation times $T_2$ and $T_1$ respectively for histidine coated SPIO nanoparticles diluted to 50 mg/L with distilled water.
Figure 4B:
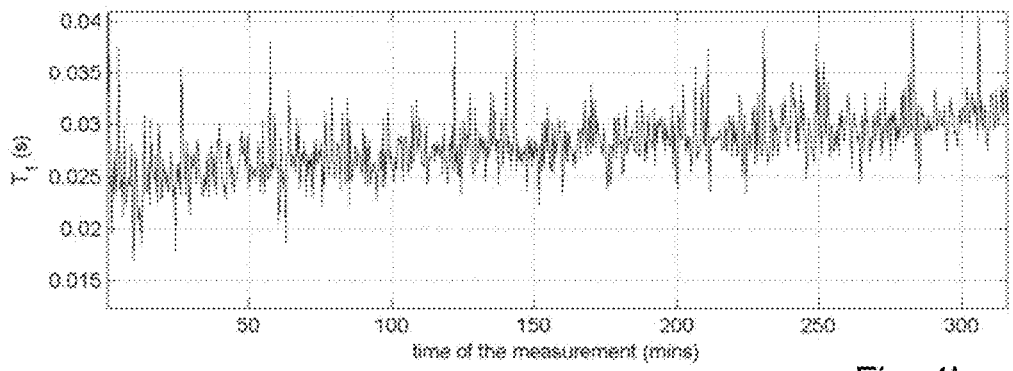

In order to determine the stability of the particles, degradation studies were carried out over a period of several hours, the results of which are shown in FIGS. 4a and 4b. Over six hours (300 minutes), measurements for both $T_1$ (FIG. 3a) and $T_2$ (FIG. 3b) were taken with an interval of 1 second between measurements. It is clear from the graph that both $T_1$ and $T_2$ relaxation times start to increase over this period of time, presumably due to degradation of the coated SPIO nanoparticles. This increase is however small, representing only an increase of 10 ms over this time period for $T_1$ and 0.8 ms for $T_2$. It is thought that the loss of signal is due to the loss of coating from the nanoparticles as an equilibrium is gradually reached with material in solution. The particles were observed to remain in suspension for 1 month at room temperature, and relaxation times were observed to remain similar after two months. Similar results to those shown in FIGS. 3a and 3b were observed in blood.

An aliquot of a 50 mg/L histidine-SPIO dispersion was evaporated to dryness under vacuum, and 24 hours later rehydrated with the same volume of distilled water. When the rehydrated amino acid-SPIO complex was tested it was found that the iron content was lower than before the dehydration, indicating that the process is not 100% efficient as not all of the complex becomes resuspended. However, the $T_1$ and $T_2$ values were around those expected for the new concentration of iron with a histidine coating. Additionally, a dry sample of SPIO particles coated with vitamin C was subjected to autoclave condition of 121° C. and 15 psi for 20 minutes. These particles were then successfully resuspended in aqueous dispersion, and TEM showed the particle morphology was maintained and had not become agglomerated.

In a further exemplary embodiment, an organic coating agent, in this case palmitic acid, was mixed with an SPIO nanoparticle powder in the same manner as described above. The mixture was then taken up, i.e. dissolved and suspended, into chloroform. The result was a brown organic solution. In further alternative embodiments, sonication was applied to a mixture of SPIO with amino acid, which was found to be ineffective. Room temperature mixing of a mixture of SPIO with amino acid was found to be effective for aspartic acid, glutamic acid and threonine. Mixing at elevated temperatures of around 60° C. was also attempted, but was found to be ineffective. Heating a mixture of SPIO and amino acid to just below the decomposition temperature of the amino acid was found to be effective for all of the amino acids with the exception of phenylalanine, which may have been due to its hydrophobic nature. However, for all of these alternative embodiments there was observed a large amount of aggregation leading to long relaxation times and very large particles as measured by TEM and DLS. From these results it was concluded that the heating method was not preferable.

In a further example, a 1:1 mass ratio of hexadecanediol and SPIO were ground together for 5 minutes using a mortar and pestle. The mixture was then taken up into chloroform, centrifuged and the supernatant filtered. Analysis by ICP indicated the presence of 151 mg/l of Fe in the sample, indicating that the hexadecanediol, and in particular the diol group, had bound to the SPIOs. Particle size analysis by DLS indicated some agglomeration but with a majority of particles around 80 nm.

As an alternative to hand mixing by mortar and pestle, grinding was also carried out using a KitchenAid® "Artisan" burr coffee grinder on mixtures of organic compounds with SPIO nanoparticles, using the grinder with the burrs at the closest setting to maximise the shearing action on the dry powder mixture. The mixture was passed through the grinder five times to yield a uniform powder. This powder was then solubilised in a solvent such as distilled water or another suitable solvent depending on the organic compound for further analysis.

In a series of experiments to determine the effect of alternative dry mixing methods, 2.00 g of SPIO and 2.00 g of HCl salt of histidine were processed either using a pestle and mortar for 5 minutes or through a coffee grinder 5 times. In each case, 100 mg samples were taken, amounting to 10 samples for each method. 5 ml of water was added to each of these samples individually and then processed through 0.2 m pore filter. Samples were diluted 1 in 10 for analysis using ICP in order to determine the homogeneity of the powders produced. The results, summarised in table 2 below, indicate that the coffee grinder method produces a more homogeneous powder, as expected from a mechanically controlled process, with a mean of 55.5 mg/l Fe content and a standard deviation of 4.1. The mortar and pestle processed powders were fairly homogeneous with a mean of 100.3 mg/l of Fe and standard deviation of 11.3.

There is a clear significant difference in the Fe content of the powders produced by the two different methods as assessed for example by the Mann Whitney U test and T-test. For the U test, $U_1=45$ and $U_2=-55$, and for the T test, $T=3.4\times10^{10}$.

TABLE 2

Experimental data comparing mortar and pestle mixing (P samples) with coffee grinding mixing (C samples).

| Sample | ppm Fe | Original ppm Fe |
|---|---|---|
| P1 | 11.55 | 115.5 |
| P2 | 8.424 | 84.24 |
| P3 | 9.415 | 94.15 |
| P4 | 11.64 | 116.4 |
| P5 | 9.675 | 96.75 |
| P6 | 9.812 | 98.12 |
| P7 | 8.988 | 89.88 |
| P8 | 9.127 | 91.27 |
| P9 | 11.16 | 111.6 |
| P10 | 10.51 | 105.1 |
| C1 | 5.31 | 53.1 |
| C2 | 4.862 | 48.62 |
| C3 | 5.402 | 54.02 |
| C4 | 5.059 | 50.59 |
| C5 | 5.558 | 55.58 |
| C6 | 5.699 | 56.99 |
| C7 | 6.212 | 62.12 |
| C8 | 5.608 | 56.08 |
| C9 | 6.096 | 60.96 |
| C10 | 5.677 | 56.77 |
| Standard Deviation | | 11.27533 |
| Mean | | 100.301 |
| Standard | | 4.179338 |

TABLE 2-continued

Experimental data comparing mortar and pestle mixing (P samples) with coffee grinding mixing (C samples).

| Deviation Mean | 55.483 |
|---|---|

According to certain embodiments, coated metal oxide particles may be suspended in a polymer matrix, for example by suspending the coated particles in a liquid polymeric precursor material prior to polymerisation. Coating materials may be used that are soluble in the polymer matrix, particular examples being paracetamol and diclofenac, which are soluble in methyl methacrylate and may be used as coating materials for SPIOs. As an example, the particles and coating material may be mixed as described above to provide a dry or solvent-free mixture. The mixture is then taken up into the monomer precursor liquid. Methyl methacrylate is a preferred example. Palmitic acid is an example of a coating material which may be applied to SPIOs and then suspended in toluene, which is miscible with many polymeric matrices. As with other examples, the suspended particles may be filtered, or centrifuged, to remove large unbound particles.

Using a polymeric matrix as the suspending medium, or solvent, once the coated particles are suspended then they will remain fixed in the matrix as it is polymerised. Methods using this technique have been trialled, as detailed above, using methyl methacrylate, which is used extensively for synthesising polymers.

As described above, a liquid coating material may be used, a preferred example being glycerol, having OH groups that enable binding to the surface of the metal oxide particles. In an example experiment, 1 g of SPIOs and 1 g (0.79 ml) of glycerol were placed in a mortar and ground with a pestle for 5 minutes. 5 ml of water was then added to this mixture before processing through a 0.2 um microfilter. A brown solution (SPIOs coated with glycerol suspended in water) was produced.

While not wishing to be bound by any particular hypothesis, it is postulated that the reason the dry mixing method described herein is effective is because the coating materials contain functional groups containing lone electron pairs which are able to donate electrons towards the particles, thus allowing these groups to associate or bind to iron oxide on the surface of the nanoparticles. This is supported by the evidence that aspartic acid and glutamic acid, both of which have two carboxyl groups containing a greater number of unbound electrons, appear to bind more readily than other amino acids. Since each have two carboxyl groups it is reasonable to assume that, in support of this hypothesis, it is the carboxylic acid groups that are responsible for the binding. The solutions from amino acids that were recrystallised remained stable for a period of 1 month, with those not recrystallised being stable for up to 3 months.

A series of comparisons were made between existing coated SPIO nanoparticles and selected examples of coated nanoparticles made according to the methods described above. Table 3 below indicates a comparison between the NMR $T_1$ and $T_2$ relaxation times for a dextran-coated SPIO nanoparticle composition (known as Endoremm, available in Europe from Guerbet S. A.) and nanoparticles coated according to the methods described herein with the amino acid histidine and the peptide P53(108). As a baseline comparison, the relaxation times for water are also given.

Baseline comparisons could alternatively be made with other NMR active nuclei, such as fluorine (which may be used in the form of a fluorocarbon gas such as hexafluoroethane, $C_2F_6$).

Table 4 below provides a further comparison of relaxation times for histidine-coated SPIO nanoparticles formed according to the methods described herein at various different stages of processing. The relaxation times increase from the as-formed values by between 2 and 3 times after 43 days. The relaxation times increase further upon dehydration followed by re-dissolving, increasing $T_1$ by around 20 times and $T_2$ by around 6 times, suggesting that not all of the SPIO particles are taken back up into solution after dehydration and re-dissolving.

TABLE 3

A comparison of NMR relaxation times with existing dextran coated nanoparticles.

| SPIO Coating | $T_1$ (ms) | $T_2$ (ms) |
|---|---|---|
| Dextran (Endorem ®) | 14.2662 | 3.0424 |
| Histidine | 9.4887 | 2.6079 |
| P53(108) | 5.7752 | 1.4897 |
| Water | ~2500 | ~100 |

TABLE 4

A comparison of NMR relaxation times for histidine-coated SPIO nanoparticles under different conditions.

| Condition | $T_1$ | $T_2$ |
|---|---|---|
| Histidine Coated SPIO | 3.3637 | 1.3399 |
| Histidine Coated SPIO + 43 days | 9.4887 | 2.6079 |
| Histidine dehydrated and redissolved | 75.4144 | 8.5825 |
| Histidine diluted in PBS (Phosphate buffered saline solution) | 1113.3641 | 14.0335 |

The following coating agents have been applied successfully to SPIO nanoparticles using the dry mixing method described herein:

All 20 naturally occurring amino acids:
Class I and Class II peptides;
Fatty acids, including palmitic acid (taken up into organic solvents such as chloroform, toluene or polymer matrices);
Antibiotics including Neomycin and Nitrofurantoin:
X-Ray imaging agent iodipamide;
Fluorescent markers such as fluorescein;
Vitamins including ascorbic acid; and
Pharmaceuticals including Diclofenac, Paracetamol and aspirin.

In the case of iodipamide, this X-ray imaging agent could advantageously be used in combination with SPIO nanoparticles to provide a combined contrast imaging agent, with the iodipamide providing X-ray imaging contrast and the SPIO providing NMR imaging contrast.

Figure 5:
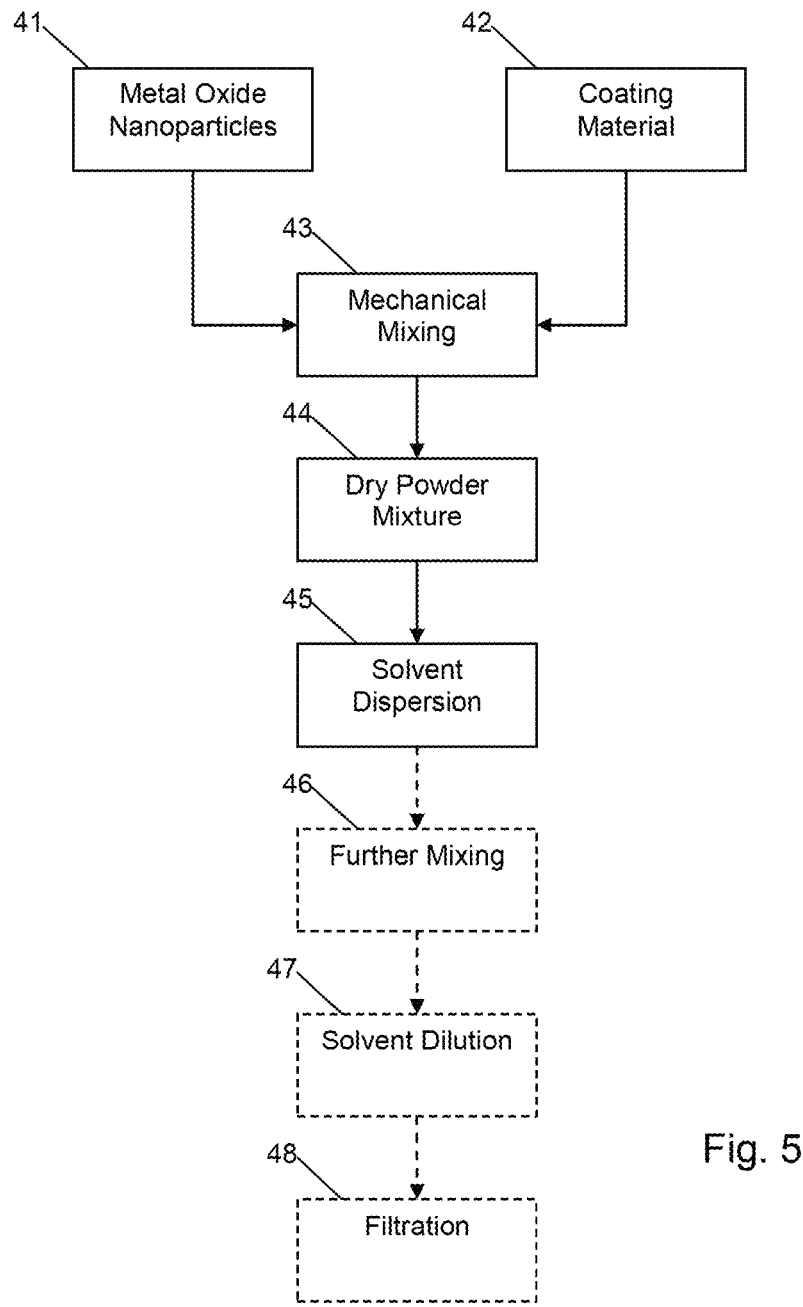
FIG. 5 is a schematic flow diagram illustrating a method according to an aspect of the invention.

Shown in FIG. 5 is a schematic flow diagram of a method according to an embodiment of the invention. A first quantity of metal oxide nanoparticles 41 and a second quantity of a coating material 42 are brought together and subjected to mechanical mixing 43. After mixing, the resulting dry powder mixture 44 may be stored or can be prepared for use by dispersing the mixture in a solvent 45. The resulting dispersion or colloid may be subjected to further mixing 46 following dispersion, and further dilution 47. The dispersion may also be subjected to filtration 48, either with or without the further mixing or dilution steps.

Figure 6:
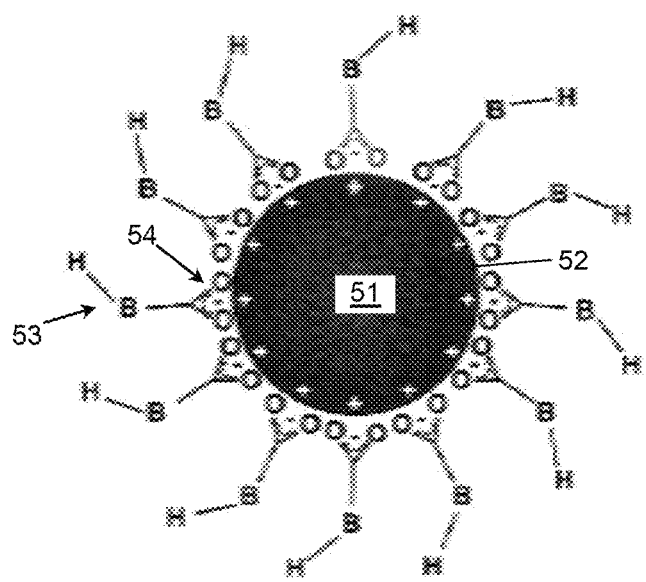
FIG. 6 is a simplified schematic diagram illustrating electrostatic bonding of organic molecules to a charged metal oxide particle.

FIG. 6 illustrates schematically in simplified form the general principle of how an organic compound, or ligand, may bond electrostatically to a metal oxide particle 51 such as a nanoparticle via one particular mechanism, in this case employing carboxyl groups. Carboxyl groups 54 (i.e. having the structure —COOH, disassociating to —COO⁻ in solution) of each molecule 53 of the organic compound are attracted to charges on the outer surface 52 of the particle 51, thereby creating a particle that is coated, or functionalised, with a selected bridging group B. Similar mechanisms apply to other groups able to dissociate in solution such as hydroxyl, amine or phosphate groups.

In conclusion, it has been demonstrated herein that potentially bioactive MRI traceable nanoparticles can be synthesised by means of a simple, solvent-free coating method. The resulting coated nanoparticle mixtures can be made readily soluble/dispersible in water or another solvent, and the resulting solution can be stable over extended periods, lending such dispersions to future development for applications in areas such as contrast agents for medical imaging.

The following sections describe experiments carried out on fortification of a food crop, namely potato, with coated iron oxide particles made according to methods similar to or the same as those described above.

A number of amino acid coatings were initially selected due to their ease of binding to the iron oxide nanoparticle and their high solubility in water. Coatings of Glutamic Acid (E), Glycine (G), Histidine (H) and Alanine (A) were selected for testing. The test consisted of submerging potato plantlets in solutions containing SPIOs coated with each amino acid and nutrients for six hours a day for 3 weeks. The concentration of Fe was kept constant at 2 mg/l for each coating system, as measured by ICP-OES (Inductively Coupled Plasma Optical Emission Spectroscopy). A control system containing just the micronutrient was also tested as a comparative study. The plantlets were then splutter coated with gold and the location and concentration of Fe in the roots of the plantlets was measured using SEM-EDX (scanning electron microscopy, energy dispersive X-ray spectroscopy.

1 ml of Histidine coated SPIOs were added to 4 ml of buffer solutions of differing pH. (pH=2, 4, and 5). The solutions were then placed onto an MRI MOUSE and their $T_1$ and $T_2$ relaxation signals measured every 30 minutes over a 24 hour period. After completion of one complete growth cycle, samples of the feed solution from The tanks were taken and their $T_1$ and $T_2$ relaxation signals were measured. The data was normalised for each starting concentration then compared.

For preparation of the iron oxide particles, two solutions, one containing both Fe(II) (1.97 mol dm⁻³) and Fe(III) (3.08 mol dm⁻³) and the other containing $NH_3$ solution, were pumped into a spinning disc reactor at 46 ml/min and 55 ml/min respectively. The resultant solution was then filtered and the solid washed once with ethyl acetate then twice with water. The resulting SPIOs were dried in a vacuum oven overnight at 40° C. and 0.1 mmHg (0.13 mbar). Once dried the SPIO's were then ground with equivalent mass of Histidine in a mortar and pestle, dissolved in distilled water. The solutions were centrifuged and the supernatant passed through a 0.02 μm syringe filter. The SPIO solutions were then analysed by ICP to measure their iron content, then added to the hydroponic tanks to obtain the correct concentration.

In order to test the hypothesis that iron oxide nanoparticles could be utilised to increase the iron concentration in plants, a system to grow plants in an environment that exposes them to coated iron oxide nanoparticles was developed. The plant targeted for enrichment was potatoes (*solanum tubersum*) due to their quick growth cycle and being a staple crop naturally low in iron.

Growth conditions were as follows:
5 day seedling establishment
Optimum air temp (light/dark): 20/16° C.
Photosynthestic photon flux: 500-800 µmol m$^{-2}$ s$^{-1}$
Photoperiod (light/dark): 12/12 hrs
Duration of growth: 63-84 days A hydroponic system was used to enable a high degree of control over the crop growing conditions. The system consisted of a reservoir for holding the nutrient solution, which was pumped into a growth medium (clay pellets) at six hour intervals with a constant flow rate of 100 ml/min. A set amount of nutrient was added to the reservoir at the beginning of the plant growth cycle, as indicated in Table 1 below, with the levels monitored via conductivity readings and maintained by the addition of a refill solution (see Table 2 below) added when needed. The pH of the nutrient solution was monitored and kept constant through the addition of $HNO_3$ and KOH to prevent biasing of results. Six hydroponic systems were used, each containing eight individual potato plants. Different concentrations of coated iron oxide nanoparticles were added to the reservoirs of each system (see Table 3 below). Each plantlet was wrapped in fiberglass then placed into the clay pellet media at a depth of 5 cm. The fiberglass was used to help anchor the plant and maintain a moist environment.

Every two days the height and number of stems for each plant was recorded, and every week the conductivity of the tank solutions measured and nutrient solution added when needed. On completion of one full growth cycle each plant was removed from the system, divided into roots, tubers and leaves. Each component was then weighed, the roots and leaves dried by hanging in a well-ventilated room for 2 weeks then weighed again to obtain the biomass. The tubers were washed with distilled water to remove any residue then taken for analysis straight away without any drying.

TABLE 1

Composition of start-up nutrient.

| Nutrients | $M_r$ | mol/l | g/l |
|---|---|---|---|
| $KNO_3$ | 101.1032 | 0.0025 | 0.252758 |
| $Ca(NO_3)_2$ | 164.088 | 0.00 | 0.41022 |
| $MgSO_4$ | 120.366 | 0.001 | 0.120366 |
| $KH_2PO_4$ | 136.086 | 0.0005 | 0.068043 |
| $H_3BO_3$ | 61.83 | 9.50E-06 | 0.000587385 |
| $MnCl_2 \cdot 4H_2O$ | 197.9052 | 7.40E-06 | 0.001464498 |
| $ZnSO_4 \cdot 7H_2O$ | 287.5799 | 9.60E-07 | 0.000276077 |
| $CuSO_4 \cdot 5H_2O$ | 249.6861 | 5.20E-07 | 0.000129837 |
| $FeCl_3 \cdot 6H_2O$ | 270.2957 | 5.00E-05 | 0.013514784 |
| $(NH_4)_6Mo_7O_{24}$ | 1235.873 | 1.00E-08 | 1.23587E-05 |

TABLE 2

Composition of refill nutrient.

| Nutrients | $M_r$ | mol/l | g/l |
|---|---|---|---|
| $KNO_3$ | 101.1032 | 4.60E-02 | 4.6507472 |
| $Ca(NO_3)_2$ | 164.088 | 0.01 | 1.969056 |
| $MgSO_4$ | 120.366 | 1.00E-02 | 1.20366 |
| $KH_2PO_4$ | 136.086 | 5.60E-02 | 7.620816 |
| $H_3BO_3$ | 61.83 | 1.23E-04 | 0.00760509 |
| $MnCl_2 \cdot 4H_2O$ | 197.9052 | 7.40E-06 | 0.001464498 |
| $ZnSO_4 \cdot 7H_2O$ | 287.5799 | 1.25E-05 | 0.003594749 |
| $CuSO_4 \cdot 5H_2O$ | 249.6861 | 6.80E-06 | 0.001697865 |
| $FeCl_3 \cdot 6H_2O$ | 270.2957 | 1.34E-04 | 0.036219621 |
| $(NH_4)_6Mo_7O_{24}$ | 1235.873 | 1.30E-07 | 0.000160663 |

TABLE 3

Concentration of Fe added to hydroponic systems.

| System number | Concentration of Fe in SPIOs (mg/l) |
|---|---|
| 1 (control) | 0 |
| 2 | 4 |
| 3 | 8 |
| 4 | 6 |
| 5 | 10 |
| 6 | 12 |

Three tubers from each system were selected, individually weighed then placed in separated beakers containing 50 ml nitric acid. After one week 10 ml of the digested solution was taken from each sample and centrifuged for 20 min at −5° C. 1 ml of the supernatant liquids were pipetted into 100 ml volumetric flasks which were made up with distilled water. The iron concentration for each sample was then determined by ICP-OES analysis (see Table 4 below) using calibration standards of known concentration. The same process was undertaken on the leaves (see Table 5) also.

TABLE 4

Results for the ICP of tubers

| Concentration of SPIO/ mg/l | Weight of potato/g | Concentration of Fe in sample/mg/l |
|---|---|---|
| 0 | 56.5 | 0.543106814 |
| 0 | 60.023 | 0.477673034 |
| 0 | 54.24 | 0.52944677 |
| 2 | 29.79 | 0.7667198 |
| 2 | 21.226 | 0.532051984 |
| 2 | 23.46 | 0.5834565 |
| 4 | 63.283 | 0.727932931 |
| 4 | 40.723 | 0.514716368 |
| 4 | 47.58 | 0.6123025 |
| 8 | 49.48 | 0.633362267 |
| 8 | 46.61 | 0.544922282 |
| 8 | 47.11 | 0.589757213 |
| 10 | 43.39 | 0.665625176 |
| 10 | 30.67 | 0.576235819 |
| 10 | 32.64 | 0.73934673 |
| 12 | 32.12 | 0.749311017 |
| 12 | 28.8 | 0.620396841 |
| 12 | 29.1 | 0.73446793 |

TABLE 5

Results for the ICP of leaves

| Concentration of SPIO/mg/l | Concentration of Fe in leaves/mg/l |
|---|---|
| 0 | 0.096783212 |
| 0 | 0.131991014 |
| 0 | 0.081605692 |

TABLE 5-continued

Results for the ICP of leaves

| Concentration of SPIO/mg/l | Concentration of Fe in leaves/mg/l |
|---|---|
| 2 | 0.104911768 |
| 2 | 0.104409204 |
| 2 | 0.095542743 |
| 4 | 0.089893508 |
| 4 | 0.085751001 |
| 4 | 0.089489036 |
| 8 | 0.167328166 |
| 8 | 0.079586658 |
| 8 | 0.091180773 |
| 10 | 0.086170141 |
| 10 | 0.088076948 |
| 10 | 0.096664607 |
| 12 | 0.087535319 |
| 12 | 0.09425815 |
| 12 | 0.128639972 |

Ten tubers from each different concentration were placed in a Bruker BioSpec small bore scanner and there $T_1$ and $T_2$ relaxations were measured and recorded.

For starch analysis, 0.1-0.5 g of each sample potato was homogenized in hot 80% ethanol to removed sugars. The solution was centrifuged and the residue retained. The solid was then washed 3 times with hot ethanol until the washing give no colour when added to an Anthrone reagent (comprising 200 mg of Anthrone dissolved in 100 ml of ice cold 95% sulphuric acid). Water (5 ml) and 52% perchloric acid was added to the residue, which was left to stand at 0° C. overnight. The solutions were then centrifuged again and the supernatant retained. The extraction was repeated again and the supernatants for each samples pooled and made up to 100 ml in volumetric flasks. 0.1 ml of the supernatants were then pipetted into a conical flask and made up to 1 ml with water.

Glucose standards were prepared by taking different volumes of the working standard (0.2, 0.4, 0.6, 0.8 and 1.0 mL) and diluting up to 1 ml. 4 ml of the Anthrone reagent was added to both the test samples and the standards, which were then boiled for 8 minutes. Once boiled, the samples were cooled in an ice bath. The intensity of the peak at 630 nm was measured (see Table 6) and compared to known standards.

TABLE 6

Results for starch analysis of tubers.

| Concentration of SPIO/mg/l | Intensity of Uv-vis peak at 630 nm |
|---|---|
| 0 | 0.83079 |
| 0 | 1.00285 |
| 0 | 0.9361 |
| 4 | 1.186 |
| 4 | 0.9761 |
| 4 | 0.9848 |
| 6 | 1.05581 |
| 6 | 1.00764 |
| 6 | 0.84334 |
| 8 | 0.86615 |
| 8 | 0.8433 |
| 8 | 0.87186 |
| 10 | 0.93023 |
| 10 | 0.80433 |
| 10 | 0.8287 |
| 12 | 0.93023 |
| 12 | 0.80433 |
| 17 | 0.8287 |

A number of amino acid coatings were selected due to their ease of binding to the iron oxide nanoparticle and their high solubility in water. The coatings: E, G, H and A were the first four of these coating systems to be screened in a preliminary test. This test consisted of submerging potatoes plantlets in solutions containing SPIOs coated with each amino acid and nutrients, for six hours a day for 3 weeks. The concentration of Fe was kept constant at 2 mg/l for each coating system, measured by ICP-OES (Inductively Coupled Plasma Optical Emission Spectroscopy). A control system containing just the micronutrient was also tested as a comparative study.

ICP analysis showed the plantlet submerged in Histidine and Glutamic acid coated SPIOs contained a higher concentration of iron per mass then the control. SEM (Scanning Electron Microscopy) analysis showed a higher Fe concentration in the roots of the plantlets exposed to the Histidine coated SPIOs compared with the control plantlet and the glutamic acid coated SPIO treatment.

TABLE 7

EDS elemental analysis of plantlets exposed to histidine-coated SPIOs

| Element | Weight % | Atomic % |
|---|---|---|
| C | 60.27 | 69.40 |
| O | 32.82 | 28.37 |
| P | 1.96 | 0.88 |
| Ca | 1.26 | 0.43 |
| Fe | 3.69 | 0.91 |

TABLE 8

EDS elemental analysis of control plantlet

| Element | Weight % | Atomic % |
|---|---|---|
| C | 64.54 | 71.76 |
| O | 32.36 | 27.01 |
| P | 2.08 | 0.90 |
| Ca | 0.96 | 0.32 |
| Fe | 0.05 | 0.01 |

Due to these results histidine was selected as the coating for the first hydroponic trial.

SPIOs were prepared using the co-precipitation of ferrous and ferric salt solutions with aqueous ammonia solution in a spinning disc reactor. The main components of the SDR are: a rotating ridged disc with 100 mm diameter with controllable speed, a feed system capable of pumping solutions onto the centre of the disc and a glass walled housing for the disc, with drainage to facilitate recovery of the SPIO product. The solutions produced by processing through the SDR were filtered then washed to isolate the SPIO product. This solid was then dried under vacuum and coated with Histidine via grinding with a mortar and pestle. The concentration Fe in the coated-SPIOs was measured using ICP-OES.

Investigation into the effect of disc rotation speed found that 2000 rpm was the optimum spin speed for the SDR. At this speed the nano-particles produced were 10 nm in diameter and very uniform (FIG. 13). Below this spin speed a secondary particle morphology, was observed, these were rod like structures (FIG. 14) with larger diameters, possibly the result of residual chlorine salts present in the reaction mixture. Spin speeds above 2000 rpm shown no further increase in particle size. Due to these results all SPIOs used in the following experiments were made at 2000 rpm.

As plants release organic acids into the rhizosphere in order to facilitate uptake of minerals, to ascertain if these changes in pH would affect the stability of the iron oxide nanoparticles, known concentrations of coated SPIO was added to a number of buffer solutions and their $T_2$ relaxation time was measured over a period of 24 hours. If the SPIOs coating were disrupted by the buffer solution the iron oxide would drop out of solution and an increase in relaxation time would be observed. Buffers with a pH of 2, 4 and 6 were selected as they are analogous to pH changes found around the roots of plants. The results showed no significant change in relaxation time in any of the pH ranges tested which suggests that the coated SPIOs are stable in the tested pH range.

The coated SPIOs were added at different concentrations (4 ppm, 6 ppm, 8 ppm, 10 ppm, 12 ppm) to the feed tanks of the hydroponic systems. The height of each plant in the six tank systems was measured every two days. FIG. 6 shows the average plant height in each tank over time, indicating that increasing SPIO concentrations have a positive effect on the overall growth rate of the potato plants. This result implies that there must be some level of interaction between the coated-SPIOs and the plant. The plants showed no external signs of iron toxicity e.g. leaf discoloration even at the highest concentration which suggests the iron absorbed is being effectively stored. The measurements for the 8, 10 and 12 ppm tanks had to be aborted early, due to a pump malfunction damaging the plants and forcing early harvest. The tubers harvested increased in size as the coated SPIO concentration increased, which reinforces the hypothesis that there is a positive interaction between SPIO and plant. To investigate if any SPIO was observed in the tubers produced MRI experiments were conducted.

FIG. 9 illustrates the effect of SPIO on potato plant growth rate. The results for C=0 represent the control tank, C=4 corresponds to 4 ppm of coated SPIO added, C=6 corresponds to 6 ppm of coated SPIO added, C=8 8 ppm of coated SPIO added, C=10 10 ppm of coated SPIO added, and C=12 12 ppm of coated SPIO added. The results show a positive correlation between SPIO concentration and average plant height. For results in excess of 44 days, the difference between average plant height for the control and C=6 concentrations is up to around 10 cm, or around 20%. For results around 28 days the difference for the control and C=10 concentrations is around 15 cm, or an increase of over 100% in height.

To observe if any coated-SPIO were deposited in the tubers of the plant, 10 tubers from each concentration range were placed in a Bruker Bio spec small bore MRI machine and their $T_2$ relaxation times were measured. The results, shown in FIG. 10, showed that no SPIO were observed for concentration ranges of 4 ppm 72 or 6 ppm 73. If the SPIOs were present in the potatoes the $T_2$ relaxation time should have reduced compared to the control 71. However, measurements of the average $T_2$ relaxation time of each concentration resulted in an increase in the relaxation signal observed. This is illustrated in FIG. 11, which shows the average standard deviation of $T_2$ distributions as a function of added SPIO concentration, showing results for 60 days growth 81 and 40 days growth 82. This is thought to be caused by there being more loosely bound water in the tubers, possibly as a result of osmosis effects. Higher concentrations of Fe ions in the tuber may therefore result in the plant absorbing more water to dilute it.

MRI mouse analysis of the tank solutions after complete growth cycles showed no SPIO in solution the only signal found being identified as water. $T_1$ and $T_2$ relaxation times for the solution are illustrated in FIGS. 12 and 13. This meant all the coated SPIO added to the tanks had either been absorbed by the plant or had decomposed to $Fe^{+2}$ and $Fe^{+3}$ ions. Since the pH testing mentioned above indicated that the coated SPIOs were not sensitive to changes in pH it is reasonable to hypothesise that other possible interactions must be responsible for the degradation of the SPIO coating, possibly the electrostatic attraction between the negatively charged SPIO surface and the positively charged root surface. To investigate if any of the iron from the SPIO had absorbed into the plant at all, iron content of the leaves and tubers of the potatoes plants from each concentration were measured.

To analyse the Fe content of the leaves, three 5 g portions of leaves were removed from plants in each concentration range and digested in 50 ml of concentrated nitric acid over 5 days. The solutions were then centrifuged and 1 ml of the supernatant taken, diluted and the Fe concentration measured using ICP-OES. The results showed no change in the concentration of Fe with increasing concentration of coated-SPIO, as indicated in FIG. 14. This result was expected because Fe in the leaves is essential for photosynthesis and formation of chloroplasts and therefore its concentration is highly regulated in this location, so it was unlikely that any excess Fe would be stored there.

The concentration of Fe in the tubers was tested in the same way as the leaves, ie by digestion of a known mass of potato in a known volume of acid. Testing began by utilising only cores samples of potatoes, however the results were inconclusive so whole potatoes were then used instead to gain more accurate concentration reading. These results, illustrated in FIG. 15, show a positive correlation between Fe concentration in the tuber and concentration of coated SPIO added to the feed. This suggests that the Fe from the SPIO is being transported into the plant and stored in the tubers. To investigate whether this increase of Fe in the tuber had any effect on the quality of the potato, testing into the starch content of the potatoes was also undertaken.

Starch is the main energy store for a plant, and occurs in plants as water-insoluble granules. Starch granules contain two different sort of glucose polymers known as amylose and amylopectin. Starch is the most important carbohydrate used for food and feed purposes and represents the major resource for our diet. An increase in starch content in potatoes would therefore be potentially highly beneficial. To analysis the starch content of the potatoes, Anthrone reagent was used. The samples were washed with hot ethanol to remove sugars then digested in acid, diluted in water and then added to 4 ml of Anthrone reagent. The intensity of the peak at 630 nm was then recorded of each sample then the starch content calculated using calibration against a known series of glucose concentrations. The results of the test, shown in FIG. 16, indicate a positive correlation between the amount of starch present and an increasing coated SPIO concentration.

FIG. 17 illustrates the correlation between iron concentration 171 (60 days), 172 (40 days) and starch content 173 (60 days), 174 (40 days) of potatoes grown according to the methods above as a function of iron content in solution. Both quantities increase with increasing coated SPIO concentration, suggesting that they may be related. While not wishing to be bound by any particular theory, this could be due to the fact that Fe—S clusters are used in the Oxidative phosphorylation metabolic pathway for the synthesis of adenosine triphosphate (ATP). In the plant ATP is converted into ADP by ATPases and ADP is a major component in the biosynthesis of starch. It can therefore be postulated that an increase in iron concentration in the tuber would result in an increased starch content. This higher starch content could explain the observed increase in tuber size.

The results, as described above, indicate that iron oxide nanoparticles can be used to fortify potatoes through being incorporated via a growth medium. It is expected that the same or similar mechanism for fortification may be used for other trace elements such as selenium, magnesium or zinc, which may also be prepared in the form of nanoparticles coated with a suitable organic compound such as an amino acid. It has been shown that potato plants grown in the presence of a suspension of coated iron oxide particles results in an increase in the iron content of the resulting tubers, together with a surprising additional effect of an increase in the starch content of the tubers. The advantage of using iron oxide nanoparticles may therefore be not only in increasing the amount of iron in the food crop but also in the calorific quality of the food crop.

Other embodiments are intentionally within the scope of the invention as defined by the appended claims.

What is claimed is:

1. A method of forming electrostatically coated particles for fortifying food crops or for drug or compound delivery into a body, the method comprising:
   providing a first quantity of dry, solvent-free metal oxide particles;
   providing a second quantity of a dry, solvent-free coating material comprising an organic compound; and
   mechanically mixing the metal oxide particles with the coating material in a dry, solvent-free mixing process to provide a mixture comprising the metal oxide particles electrostatically coated with the organic compound;
   wherein the mixing process is performed at a temperature of no more than 60 degrees C.

2. The method of claim 1 wherein the metal oxide particles comprise iron oxide.

3. The method of claim 1 wherein the mixing process comprises applying shear to mix the metal oxide particles and the coating material in a grinding process.

4. The method of claim 1 wherein the organic compound comprises an amino acid.

5. The method of claim 1 comprising a further step of dispersing the mixture in a solvent to provide a colloid of the electrostatically coated particles in the solvent.

6. The method of claim 5 comprising a further step of a wet mixing process to disperse the mixture in the solvent.

7. The method of claim 1 comprising a further step of dispersing the electrostatically coated particles in a polymer precursor followed by polymerisation of the polymer precursor.

8. The method of claim 1 wherein the electrostatically coated particles have a volumetric mean particle size of between 2 nm and 100 nm in diameter.

9. The method of claim 1 wherein the mixing process comprises applying shear to mix the metal oxide particles and the coating material in a milling process.

10. The method of claim 1 wherein the organic compound comprises a peptide.

11. The method of claim 1 wherein:
    the metal oxide particles comprise iron oxide;
    the mixing process comprises applying shear to mix the metal oxide particles and the coating material in a grinding or milling process;
    the method further comprises a step of dispersing the mixture in a solvent to provide a colloid of the electrostatically coated particles in the solvent;
    the method further comprises a wet mixing process to disperse the mixture in the solvent; and
    the method further comprises a step of dispersing the electrostatically coated particles in a polymer precursor followed by polymerisation of the polymer precursor.

12. A method of fortifying a food crop with a trace element, the method comprising:
    forming coated particles by:
       providing a first quantity of dry, solvent-free metal oxide particles;
       providing a second quantity of a dry, solvent-free coating material comprising an organic compound; and
       mechanically mixing the metal oxide particles with the coating material in a dry, solvent-free mixing process to provide a mixture comprising the metal oxide particles electrostatically coated with the organic compound wherein the dry, solvent-free mixing process is performed at a temperature of no more than 60 degrees C. and the metal oxide particles have a volumetric new particle size of between 2 nm and 100 nm in diameter; and
    subsequently growing the food crop in a growth medium comprising the coated particles.

13. The method of claim 12 wherein the trace element is iron in the form of iron oxide particles.

14. The method of claim 12 wherein the organic compound comprises an amino acid.

15. The method of claim 12 wherein the food crop is a tuberous, crop.

16. The method of claim 12 wherein the food crop is grown hydroponically, the metal oxide being provided as a suspension in a feed solution.

17. The method of claim 12 wherein the organic compound comprises a vitamin.

18. The method of claim 12 wherein the organic compound comprises a peptide.

19. The method of claim 12 wherein the organic compound comprises a pharmaceutical compound.

20. The method of claim 12 wherein the organic compound comprises an imaging agent.

* * * * *